United States Patent [19]
Ulrich

[11] Patent Number: 6,087,377
[45] Date of Patent: *Jul. 11, 2000

[54] TAMOXIFEN AS A THERAPY TO REDUCE IRINOTECAN HYDROCHLORIDE-INDUCED DIARRHEA

[75] Inventor: Roger G. Ulrich, Gurnee, Ill.

[73] Assignee: Pharmacia & Upjohn Company, Kalamazoo, Mich.

[ * ] Notice: This patent is subject to a terminal disclaimer.

[21] Appl. No.: 09/329,554

[22] Filed: Jun. 10, 1999

Related U.S. Application Data

[63] Continuation of application No. 09/028,779, Feb. 24, 1998, Pat. No. 5,955,466
[60] Provisional application No. 60/039,185, Feb. 27, 1997.
[51] Int. Cl.$^7$ ...................... A61K 31/445; A61K 31/135
[52] U.S. Cl. ............................................ 514/324; 514/648
[58] Field of Search ..................................... 514/648, 324

[56] References Cited

U.S. PATENT DOCUMENTS

| | | | |
|---|---|---|---|
| 4,536,516 | 8/1985 | Harper et al. | 514/514 |
| 4,604,463 | 8/1986 | Miyasaka et al. | 544/125 |

FOREIGN PATENT DOCUMENTS

| | | |
|---|---|---|
| 96/01127 | 1/1996 | WIPO . |

OTHER PUBLICATIONS

Jaiyesimi, IA, et al.; Use of Tomoxifen for Breast Cancer: Twenty–Eight Years Later, *J. Clin. Oncol.* 13:513–529, 1995.

Gould, K., et al.; Breast Cancer Prevention: A Summary of the Chemoprevention Trial with Tomoxifen, *Oncol. Nurs. Forum.* 21:835–840, 1994.

Otto, AM., et al.; Cell–cycle Arrest, Micronucleus Formation, and Cell Death in Growth Inhibition of MCF–7 Breast Cancer Cells by Tamoxifen and Cisplatin, *J. Cancer Res. Clin. Oncol.* 122:603–612, 1996.

Watts, CKW., et al.; Antiestrogen Inhibition of Cell Cycle Progression in Breast Cancer Cells is Associated with Inhibition of Cyclin–Dependent Kinase Activity and Decreased Retinoblastoma Protein Phosphorylation, *Mol. Endocrin.* 9:1804–1813, 1995.

*Primary Examiner*—Raymond Henley, III
*Attorney, Agent, or Firm*—McDonnell Boehnen; Hulbert & Berghoff

[57] ABSTRACT

The present invention provides a method for preventing or decreasing diarrhea associated with irinotecan administration comprising the administration of tamoxifen at least two cell cycles prior to irinotecan administration.

8 Claims, No Drawings

TAMOXIFEN AS A THERAPY TO REDUCE IRINOTECAN HYDROCHLORIDE-INDUCED DIARRHEA

CROSS-REFERENCE TO RELATED APPLICATIONS

This application is a continuation of U.S. application Ser. No. 09/028,779 filed Feb. 24, 1998, now U.S. Pat. No. 5,955,466, which claims the benefit of provisional application U.S. Ser. No. 60/039,185, filed Feb. 27, 1997, under 35 USC 119(e)(i).

BACKGROUND OF THE INVENTION

The present invention provides a new use of known pharmaceutical compounds. In particular the present invention provides a method for reducing the side effects associated with anticancer drug irinotecan by the prior coadministration of anticancer drug tamoxifen.

In humans, irinotecan hydrochloride, the active ingredient in CAMPTOSAR Injection, induces a potentially life-threatening intestinal toxicity (diarrhea). We have been studying the mechanism for this toxicity with the goal of identifying an intervention therapy. In previous hamster studies we found irinotecan to block intestinal epithelial cells in the $G_2$ phase of the cell cycle concurrent with the onset of diarrhea). We believe this $G_2$ block reduces intestinal epithelial cell differentiation (a $G_1$-associated process), resulting in a loss of physiological function and the onset of diarrhea. Based on our findings, we claim that blocking normal epithelial cells in $G_0/G_1$ would prevent entry into S phase and thus protect these cell against CPT-11 (SN-38) toxicity. Tamoxifen, a marketed antiestrogen chemotherapeutic agent, is known to induce a block in the $G_0/G_1$ phase of the cell cycle.

As seen below, we show that tamoxifen: 1) enhances the recovery of a non-tumor cell line from SN-38-induced inhibition but enhances the toxicity of SN-38 in a tumor cell line; 2) reduces weight loss attributable to diarrhea in hamsters treated with CFT-11, 3) reduces the colonic pathology and physiological effects induced in the hamster by CPT-11. These findings indicate a potential therapeutic benefit in coadministration of tamoxifen as a protective agent prior to and along with CPT-11.

INFORMATION DISCLOSURE

Tamoxifen is a nonsteroidal antiestrogen with activity in the treatment (Jaiyesimi I A, Buzdar A U, Decker D A, Hortobagyi G N. Use of tamoxifen for breast cancer: twenty eight years later. J Clin Oncol 1995;13:513–529.) and perhaps prevention (Gould K, Gates M L, Miaskowski C. Breast cancer prevention: a summary of the chemoprevention trial with tamoxifen. Oncol Nurs Forum 1994;21:835–840.) of breast cancer. Unlike most chemotherapeutics, which act in the S, $G_2$ and M phases of the cell cycle, tamoxifen clearly blocks cell cycle progression in $G_0/G_1$ (Otto A M, Paddenberg R, Schubert S, Mannherz H G. Cell cycle arrest, micronucleus formation, and cell death in growth inhibition of MCF-7 breast cancer cells by tamoxifen and cisplatin. J Canc Res & Clin Oncol 1996;122:603–612). This is thought to be through repression of $G_1$-specific protein kinase activity (cyclin D1/cdk4; Watts C K W, Brady A, Sarcevic B, Defazio A, Musgrove E A, Sutherland R L. Antiestrogen inhibition of cell cycle progression in breast cancer cells is associated with inhibition of cyclin dependent kinase activity and decreased retinoblastoma protein phosphorylation. Mol Endocrin 1995; 9:1804–1813).

Published PCT application WO/96/01127, published Jan. 18, 1996, discloses a wide variety of agents to be co-administered with irinotecan, including tamoxifen. However, it does not disclose prior administration of tamoxifen.

SUMMARY OF THE INVENTION

The present invention particularly provides a method for preventing or reducing diarrhea associated with irinotecan therapy in a patient suffering from or susceptible to said diarrhea comprising the administration to said patient of an effective amount of tamoxifen at least two cell cycles prior to administration of the irinotecan.

The preparation and use of irinotecan is known (see U.S. Pat. No. 4,604,463 which is expressly incorporated by reference herein). It is available commercially in the form of CAMPTOSAR Injection, sold by Pharmacia & Upjohn. The preparation and use of tamoxifen citrate is also well known (see U.S. Pat. No. 4,536,516, which is expressly incorporated by reference herein). This is commercially available as the active ingredient in NOLVADEX which sold by Zeneca.

The topoisomerase I inhibitor irinotecan hydrochloride; an analogue of camptothecin has shown activity against a variety of tumor types, and in particular refractory colorectal tumors. The major dose-limiting toxicity in cancer patients is a severe delayed chronic grade 3–4 diarrhea. Though somewhat manageable by existing means, therapeutic intervention to reduce or prevent chronic diarrhea in patients would allow for more intensive irinotecan treatment strategies and increased patient comfort.

Mechanistic studies in the Syrian hamster have demonstrated irinotecan to produce considerable toxicity to the intestinal epithelium that is coincident with the onset of delayed diarrhea. This toxicity was characterized histologically by a time-dependent loss of structural integrity of the mucosal epithelium in the jejunum and ileum; villi appeared corrugated and epithelial cells lost their typical columnar morphology. The epithelium of the colon appeared thinned and vacuolated. There was an apparent reduction of crypts and/or a loss of epithelial cells. Using Western immunoblot techniques, a time-dependent elevation in proliferating cell nuclear antigen (PCNA) was detected as early as day 1. Immunohistochemistry for PCNA showed an increase in the number of labelled epithelial cells and labelling intensity in treated animals, with labelled cells positionally located farther towards the villus tip compared to controls. The increased levels of PCNA and loss of differentiated cell morphology indicated that irinotecan induced a cell cycle block in $S/G_2$ with a subsequent loss of physiological (differentiated, $G_1$) function in hamster intestinal epithelium. This conclusion was further supported by studies indicating a reduction in crypt cell replication (detected by decreased bromodeoxyuridine labelling) and increased apoptosis (unpublished observations). Structural and biochemical changes in the intestinal epithelium were coincident with increased water and electrolyte loss. Additionally, in vitro studies with SN-38, the active metabolite of irinotecan, have shown HT-29 human adenocarcinoma cells to arrest in $G_2/M$ followed by apoptosis (Bacon J A, Y Maruyama, R F Kletzien, L A Foellmi-Adams, and R G Ulrich. Cell cycle inhibition and apoptosis induced by a topoisomerase inhibitor, irinotecan. J. Cell Biol., 1996 (Abstract)). By contrast, normal WI-38 human fibroblasts were arrested in $S/G_2$. Collectively, these studies indicate that irinotecan blocks cell replication in the $S/G_2$ phase of the cell cycle and that this block in the intestinal epithelial crypts leads to altered intestinal morphology and physiology.

A variety of strategies for the control of diarrhea have been examined in humans and in animal models. In humans, aggressive high-dose co-therapy with loperamide (an agent that slows intestinal motility and affects water and electrolyte movement through the bowel) has been has been used to reduce or control diarrhea (Rougier P, Bugat R. CPT-11 in the treatment of colorectal cancer: clinical efficacy and safety profile. Semin Oncol 1996;23(Suppl 3):34–41.) Though successful in most cases, this agent requires administration at 2 hr intervals at the onset of diarrhea and is not used prophylactically. The Chinese herbal medicine, kampo, has also been shown to control diarrhea in rats and humans. (See,e.g., Takasuna K, Kasai Y, Kitano Y, Mori K, Kobayashi R, Hagiwara T, Kakihata K, Hirohashi M, Nomura M, Nagai E, et al. Protective effects of kampo medicines and baicalin against intestinal toxicity of a new anticancer camptothecin derivative, irinotecan hydrochloride (CPT-11), in rats. Jpn J Cancer Res. 1995;86:978–984; and, Sakata Y, Suzuki H, Kamataki T. Preventive effect of TJ 14, a kampo (Chinese herb) medicine, on diarrhea induced by irinotecan hydrochloride (CPT-11). Gan To Kagaku Ryoho 1994;21:1241–1244.) Though the mechanism is not clearly defined, the anti-diarrheal activity of kampo is thought to be through inhibition of beta-glucuronidase. This enzyme is responsible for the deconjugation of the glucuronide form of the active irinotecan metabolite, SN-38. Deconjugation of the SN-38 glucuronide is thought to release active SN-38 back into the intestinal lumen and produce toxic effects on the intestinal epithelium. Baicalin, one component of kampo, has similar activity. Since most of the intestinal beta-glucuronidase activity is due to microbial flora, antibiotics have been suggested to have protective effects (Takasuna K, Hagiwara T, Hirohashi M, Kato M, Nomura M, Nagai E, Yokoi T, Kamatake T. Involvement of beta-glucuronidase in intestinal microflora in the intestinal toxicity of the antitumor camptothecin derivative irinotecan hydrochloride (CPT-11) in rats. Cancer Res 1996;56:3752–3757), again through reduction of beta-glucuronidase activity. The effects of kampo medicines or other beta-glucuronidase inhibitors on SN-38 pharmacokinetics or CPT-11 efficacy are not presently known. Other experimental co-therapies for ameliorating the delayed diarrhea include the somatostatin analogue octreotide (Cascinu S. Management of diarrhea induced by tumors or cancer therapy. Curr Opin Oncol 1995;7:325–329). In summary, existing therapies are directed at reducing irinotecan-induced diarrhea through reduction of intestinal motility or prevention of SN-38 glucuronide deconjugation.

Surprisingly and unexpectedly, we have found that treatment with an agent to block or slow intestinal cell replication in the $G_0/G_1$ phase of the cells cycle, prior to the onset of DNA synthesis, would protect these cells against subsequent DNA damage and apoptosis by induced by CPT-11 in $S/G_2$. In particular, we have found tamoxifen to have this protective effect.

We claim that tamoxifen, by blocking normal replicating intestinal epithelial cells in the $G_0/G_1$ phase of the cell cycle will prevent or reduce intestinal toxicity due to subsequent CPT-11 administration. This activity would require pretreatment of the patient for a period encompassing approximately 2 cell cycles (or 48 hours), with continued co-treatment at recommended oral dose levels of 20–40 mg/day (0.4–0.8 mg/kgday). A similar protective therapeutic effect would be anticipated for other antiestrogens including droloxifene, TAT-59, and raloxifene since these compounds have a pharmacologic profile similar to tamoxifen (Jordan V C. Third annual William L. McGuire Memorial Lecture. "Studies on the estrogen receptor in breast cancer—20 years as a target for the treatment and prevention of cancer." Breast Cancer Res Treat 1995;36:267–285.) Studies with droloxifene, for example, show this antiestrogen to block cells in the $G_1$ phase of the cell cycle in a manner similar to tamoxifen ( Hasmann M, Rattel B, Loser R. Preclinical data for droloxifene. Cancer Lett 1994;84:101–116).

DESCRIPTION OF THE PREFERRED EMBODIMENTS

The present invention is seen more fully in the examples below.

SN-38-Induced Cell Cycle Arrest and Apoptosis in Tumor Cells:

Treatment of human colon adenocarcinoma HT-29 cells with SN-38 showed >90% growth inhibition ($IC_{90}$) at a concentration of 10 nM. Flow cytometric analysis of growth-arrested cells revealed that replication was blocked in the $G_2$ phase of the cell cycle. From this arrest point, cells did not recover but instead underwent programmed cell death (apoptosis). As the HT-29 cells arrested, levels of p53 were upregulated as determined by Western immunoblot techniques, likely in response to sensing DNA damage since PCNA levels were also increased. However, the p53 expressed by HT-29 cells is a mutant (inactive) form hence p21 is not upregulated; we have been unable to detect p21 in these cells. These experiments show that CPT-11 (SN-38) induces apoptosis in HT-29 cells in a p53-independent manner from the $G_2$ phase of the cells cycle.

SN-38-Induced Cell Cycle Arrest in Non-Tumor Cells

In contrast to tumor cells, WI-38 normal human diploid lung fibroblasts treated with an $IC_{90}$ of SN-38 (40 nM) were arrested in the S phase of the cell cycle as determined by flow cytometry. Cells did not undergo apoptosis, but rather slowly re-entered the cell cycle when drug was removed. Levels of p53 (wild type) were increased along with PCNA and followed by increases in p21.

Effects of Tamoxifen on Cell Replication in SN-38-Treated Cells

Normal WI-38 cells pretreated with tamoxifen prior to and during SN-38 exposure regained replication kinetics to a greater extent that those not pretreated. Tamoxifen increased the toxicity of SN-38 in tumor cells (Caco2). These data suggest that tamoxifen co-therapy may increase the therapeutic ratio of CPT-11 by increasing survival of normal proliferating cells with a possible increase in tumor cell killing efficiency.

Irinotecan Toxicity in the Hamster

We have previously demonstrated inhibition of cell replication and induction of apoptosis in the hamster intestinal epithelium by CPT-11 that is coincident with diarrhea and weight loss. When hamsters were pre- and co-treated with tamoxifen, the weight loss associated with CPT-11 administration was reduced and survival increased. In another study, tamoxifen pre-and co-treatment was shown to produce an improvement in morphology and function of the hamster colon in animals treated with CPT-11. These data indicate that tamoxifen produces improvement in vivo.

What is claimed is:

1. A method for preventing or reducing diarrhea associated with irinotecan therapy in a patient suffering from or susceptible to said diarrhea comprising the administration to said patient of an effective amount of an antiestrogen at least two cell cycles prior to administration of the irinotecan.

2. The method according to claim 1, wherein the antiestrogen is administered about 48 hours prior to irinotecan administration.

3. The method according to claim 1, wherein the antiestrogen is a member selected from the group consisting of droloxifene, TAT-59, and raloxifene.

4. A method for preventing or reducing diarrhea associated with irinotecan therapy in a patient suffering from or susceptible to said diarrhea comprising the administration to said patient of an amount of an antiestrogen at a time effective to impede intestinal epithelial cell replication in the $G_0/G_1$ phase of the cell cycle.

5. The method according to claim 4 wherein said antiestrogen is administered to said patient at least two cell cycles prior to administration of the irinotecan.

6. The method according to claim 4 wherein said antiestrogen is administered to said patient about at least 48 hours prior to administration of the irinotecan.

7. The method according to claim 4, wherein the antiestrogen is a member selected from the group consisting of droloxifene, TAT-59, and raloxifene.

8. A method according to claim 4, 5, 6, or 7 wherein said amount of antiestrogen administered to said patient is in the range of about 0.4–0.8 mg/kg/day.

* * * * *